United States Patent [19]

Reinhardt

[11] Patent Number: 5,359,127
[45] Date of Patent: Oct. 25, 1994

[54] PROCESS FOR THE PREPARATION OF ACYLOXYALKANESULFONATES

[75] Inventor: Gerd Reinhardt, Kelkheim, Fed. Rep. of Germany

[73] Assignee: Hoechst Aktiengesellschaft, Frankfurt am Main, Fed. Rep. of Germany

[21] Appl. No.: 957,447

[22] Filed: Oct. 6, 1992

Related U.S. Application Data

[63] Continuation of Ser. No. 159,669, Feb. 24, 1988, abandoned.

[30] Foreign Application Priority Data

Feb. 26, 1987 [DE] Fed. Rep. of Germany ....... 3706232

[51] Int. Cl.⁵ ............................................. C07C 261/00
[52] U.S. Cl. ........................................ 560/179; 554/92
[58] Field of Search ........................... 554/92; 560/129

[56] References Cited

U.S. PATENT DOCUMENTS

| | | | |
|---|---|---|---|
| 1,881,172 | 10/1929 | Daimler | 554/92 |
| 2,821,535 | 1/1958 | Britton et al. | 554/92 |
| 2,923,724 | 2/1960 | Anderson et al. | 554/92 |
| 3,004,049 | 10/1961 | Schenck | 260/400 |
| 3,151,136 | 9/1964 | Koczorowski et al. | 260/400 |
| 3,167,570 | 1/1965 | Bohunek et al. | 554/92 |
| 3,320,292 | 5/1967 | Cahn et al. | 554/92 |
| 3,383,396 | 5/1968 | Cahn et al. | 554/92 |
| 3,394,155 | 7/1968 | Cahn et al. | 554/92 |
| 4,405,526 | 9/1983 | Lamberti et al. | 260/400 |
| 4,499,028 | 2/1985 | Longley | 554/92 |
| 4,696,773 | 9/1987 | Lukenbach et al. | 554/92 |
| 4,790,956 | 12/1988 | Weipert et al. | 252/538 |

FOREIGN PATENT DOCUMENTS 1121045  1/1962  Fed. Rep. of Germany .

*Primary Examiner*—Marianne M. Cintins
*Assistant Examiner*—Keith MacMillan

[57] ABSTRACT

Process for the preparation of acyloxyalkanesulfonates

Process for the preparation of acyloxyalkanesulfonates of the formula $$R-\overset{\overset{\displaystyle O}{\|}}{C}-O-A-SO_3M$$

where R denotes $C_7$–$C_{21}$-alkyl or $C_7$–$C_{21}$-alkenyl, A denotes $C_2$–$C_4$-alkylene and M denotes an alkali metal atom or an alkaline earth metal atom, by esterification of carboxylic acids using salts of hydroxyalkanesulfonic acids, under mild reaction conditions, carboxylic acids of the general formula $R-CO_2H$ being esterified using a salt of the formula $HO-A-SO_3M$ in the presence of aqueous hydrochloric acid.

7 Claims, No Drawings

PROCESS FOR THE PREPARATION OF ACYLOXYALKANESULFONATES

CROSS REFERENCE TO RELATED APPLICATIONS

This application is a continuation of U.S. patent application Ser. No. 07/159,669, filed Feb. 24, 1988, now abandoned.

INTRODUCTION

Acyloxyalkanesulfonic acids and salts thereof are long-known compounds having surface-active properties, and are used inter alia, as the base material for the production of syndets.

BACKGROUND OF THE INVENTION

A number of processes have already been investigated for their preparation (J. Am. Oil Chem. Soc. 48, 657 (1971)). U.S. Pat. No. 1,881,172 and U.S. Pat. No. 2,821,535 describe the reaction of Na isethionate with fatty acid chlorides. This reaction requires the use of absolutely dry and finely powdered Na isethionate; in addition, the preparation of the fatty acid hall des from fatty acid and phosphorus trichloride is time-consuming and costly and is associated with the unavoidable production of phosphorous acid. If undistilled acid chloride is used, the final product is usually contaminated by phosphorus-containing compounds, which can lead to odor problems. Direct condensation of Na isethionate with fatty acids requires reaction temperatures of 220°–250° C. It is usually necessary to employ an excess of fatty acid in order to complete this reaction, The reaction can be carried out without a catalyst (DE 1,121,045) and the presence of zinc oxide (U.S. Pat. No. 3,320,292), zinc salts of organic acids (U.S. Pat. No. 4,405,526), boric acid (U.S. Pat. No. 2,923,724) or phosphorus-containing acids (U.S. Pat. No. 3, 004,049). When gaseous hydrogen chloride is used as the catalyst, direct esterification is possible even at 180° C. (U.S. Pat. No. 3,167,570). According to U.S. Pat. No. 3,151,136, esterification of free isethionic acid using fatty acid takes place even at 130° C., but the industrial preparation of free isethionic acid from its easily accessible salts, and the neutralization of the condensation products present difficulties. The object of the present invention is to provide a process for the preparation of salts of acyloxyalkanesulfonic acids which is easy to carry out, even on a large industrial scale, and in which a direct condensation can be carried out, even under mild reaction conditions, starting from salts of hydroxyalkanesulfonic acids and fatty acids.

SUMMARY OF THE INVENTION

Surprisingly, it has now been found that direct condensation of salts of hydroxyalkanesulfonic acids with fatty acids can be carried out with short reaction times even at temperatures below 150° C. if aqueous hydrochloric acid is employed as a catalyst in this reaction. This could not have been expected since it is known that acyloxyalkanesulfonates hydrolyze extremely readily in the presence of aqueous acids.

The invention therefore relates to a process for the preparation of salts of acyloxyalkanesulfonic acids of the formula

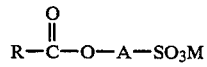

where R denotes $C_7$–$C_{21}$-alkyl or $C_7$–$C_{21}$-alkenyl, A denotes $C_2$–$C_4$-alkylene and M denotes an alkali metal atom or an alkaline earth metal atom, by reacting a carboxylic acid of the general formula R—$CO_2$H where R has the abovementioned meaning with a salt of the formula HO—A—$SO_3$M, where A is $C_2$–$C_4$-alkylene and M is an alkali metal atom or an alkaline earth metal atom, in the presence of aqueous hydrochloric acid at 80° to 150° C., and removing the water of reaction and the aqueous hydrochloric acid during the reaction by distillation.

In this reaction, the hydrochloric acid probably cleaves some of the hydroxyalkanesulfonate into the free hydroxyalkanesulfonic acid and the metal chloride. After the esterification, the acyloxyalkanesulfonic acid formed is then neutralized by the metal chloride, hydrogen chloride being liberated. At the same time, the water present in the reaction medium promotes better mixing of the reaction components and thereby makes possible a low reaction temperature and short reaction times.

In accordance with this process, a mixture of solid metal hydroxyalkanesulfonate, fatty acid and aqueous hydrochloric acid, or a mixture which is obtained from hydroxyalkanesulfonate solution and fatty acid by passing in gaseous hydrogen chloride, is warmed to 70°–120° C., preferably 90°–110° C., in order to initiate the reaction and heated with vigorous stirring while increasing the temperature to 110°–145° C., preferably 120°–135° C., in order to complete the reaction. At the same time, —expediently under reduced pressure— the aqueous hydrochloric acid and the water of reaction are removed from the reaction mixture. During the course of the reaction, the reaction mixture, which is initially non-viscous, solidifies to form a paste, from which, finally, a white solid material is formed from which the product can be obtained in powder form by comminution. It is also possible to dissolve the reaction product in water and to subsequently isolate it by spray drying. During this operation, all the hydrogen chloride remaining in the product is removed. The final product is pH neutral or slightly acid and can be corrected in pH, if necessary, by adding alkali metal carbonates or bicarbonates or alkaline earth metal carbonates or bicarbonates. The sodium chloride content of the final product is generally less than 0.5%.

DETAILED DESCRIPTION

In a particular embodiment of this process, free hydroxyalkanesulfonic acid in the concentration of up to 5 mol % can be added to the reaction mixture before or during the condensation. In addition, bleaching additives can be added to the reaction mixture.

Typical hydroxyalkanesulfonic acids which can be esterified are monohydroxyalkanesulfonic acids having 2 to 4 carbon atoms, in particular straight-chain, but also branched, 2-hydroxyalkanesulfonic acids, for example 2-hydroxyethanesulfonic acid (isethionic acid), 2-hydroxypropanesulfonic acid and hydroxybutanesulfonic acid. The hydroxyalkanesulfonic acid is employed in the form of its alkali metal salt or alkaline earth metal salt, preferably as the sodium salt. The salt can be employed in the reaction either in the solid state or as an aqueous solution. If dry hydroxyalkanesulfonate is used, aqueous hydrochloric acid is added to the reaction mixture, and, if a hydroxyalkanesulfonate solution is employed, the aqueous hydrochloric acid is expediently prepared by passing gaseous hydrogen chloride into the reaction mixture at 10°–145° C., preferably 20°–110° C. The content of hydrogen chloride in the reaction mixture at the start of the condensation should be 0.3 to 2 moles, preferably 0.6 to 1.3 moles, relative to hydroxyalkanesulfonate employed.

Typical carboxylic acids which can be employed are all straight-chain or branched carboxylic acids, in particular higher fatty acids, saturated or unsaturated, having 8 to 22 carbon atoms, such as, for example, octanoic acid, lauric acid, palmitic acid, stearic acid or mixtures thereof, such as, for example, tall oil fatty acid, tallow fatty acid or coconut fatty acid. 0.5 to 2 moles, preferably 0.8 to 1.2 moles, of a fatty acid are employed per mole of hydroxyalkanesulfonate.

The reaction time is 30 minutes to 10 hours, but preferably 1 to 4 hours.

The advantages of the direct condensation described here, in addition to high degrees of conversion, are low reaction temperatures and short reaction times. In addition, the product is free of zinc-, boron- or phosphorus-containing foreign substances, which are normally employed as catalysts in direct esterifications.

In the following examples, parts by weight are to parts by volume as the kg is to the dm$^3$, and percentages always relate to the weight—unless otherwise stated. The term SS content in the following examples is taken to mean the proportion of surface-active substance in the product, which is determined by 2-phase titration by the method of EPTON (Nature 160, 759 (1947)).

Example 1

148 parts of Na isethionate, 222 parts of hardened coconut fatty acid and 100 parts of concentrated aqueous hydrochloric acid are mixed and the mixture is heated at 100°–110° C. for 30 minutes. The temperature is subsequently increased to 130° C. over the course of 150 minutes. During this time, aqueous hydrochloric acid is removed from the reaction mixture by distillation under reduced pressure (40 mm Hg). After cooling and comminution, a white powder having an SS content of 88.6% is obtained in quantitative yield.

Example 2

148 parts of Na isethionate, 222 parts of hardened coconut fatty acid, 5 parts of isethionic acid and 100 parts of concentrated aqueous hydrochloric acid are reacted as in Example 1. When the reaction is complete, the white powder is adjusted to pH 5.5 by compounding with sodium bicarbonate. The SS content is 89.4%.

Example 3

The procedure of Example 1 is followed, except that 85 parts of concentrated aqueous hydrochloric acid are employed. A white powder having an SS content of 86.2% is obtained.

Example 4

148 parts of Na isethionate, 200 parts of lauric acid and 110 parts of concentrated aqueous hydrochloric acid are reacted analogously to Example 1. A white powder having an SS content of 90.8% is obtained.

Example 5

296 parts of technical-grade 50% strength Na isethionate solution and 222 parts of hardened coconut fatty acid are heated to 90°–110° C. HCl gas is passed into the solution for 30 minutes to make the HCl content about 1 mole. The mixture is subsequently heated under reduced pressure (40 mm) at 120° C. for 2 hours, then at 130° C. for 1 hour in order to complete the reaction. A white powder having an SS content of 87.7% is obtained.

I claim:

1. A process for the preparation of an acyloxyalkanesulfonate of the formula

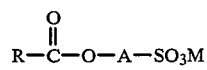

where R denotes $C_7$–$C_{21}$-alkyl or $C_7$–$C_{21}$-alkenyl, A denotes $C_2$–$C_4$-alkylene and M denotes an alkali metal atom or an alkaline earth metal atom, by esterification of a carboxylic acid using a salt of a hydroxyalkanesulfonic acid, wherein a carboxylic acid of the formula R—CO$_2$H where R has the above-mentioned meaning is esterified using a salt of the formula HO—A—SO$_3$M, where A is $C_2$–$C_4$-alkylene and M is an alkali metal or an alkaline earth metal, in the presence of aqueous hydrochloric acid, wherein the reaction is carried out at 80° C. to below 110° C. for a time between 30 minutes to 4 hours and after this time the temperature is raised to 145° C. whereby the water of the reaction and the aqueous hydrochloric acid is removed by distillation.

2. The process as claimed in claim 1, wherein 1–5 mol % of isethionic acid are added to the reaction mixture before or during the reaction.

3. The process as claimed in claim 1, wherein the content of the hydrogen chloride in the reaction mixture at the start of the esterification is 0.3 to 2 moles, relative to the salt of a hydroxyalkanesulfonic acid.

4. The process as claimed in claim 1, wherein the content of the hydrogen chloride in the reaction mixture at the start of the esterification is 0.6 to 1.3 moles, relative to the salt of a hydroxyalkanesulfonic acid.

5. The process as claimed in claim 1, wherein the water of the reaction and the aqueous hydrochloric acid is removed during the reaction by distillation under reduced pressure.

6. The process as claimed in claim 5, wherein said pressure is about 40 mm Hg.

7. The process as claimed in claim 1, wherein the resulting product has a sodium chloride content of less than 0.5%.

* * * * *